(12) United States Patent
McKnight et al.

(10) Patent No.: US 8,657,883 B2
(45) Date of Patent: Feb. 25, 2014

(54) REMOTE ACTUATED VALVE IMPLANT

(75) Inventors: Timothy E. McKnight, Greenback, TN (US); Anthony Johnson, Houston, TX (US); Kenneth J. Moise, Jr., Houston, TX (US); Milton Nance Ericson, Knoxville, TN (US); Justin S. Baba, Knoxville, TN (US); John B. Wilgen, Oak Ridge, TN (US); Boyd McCutchen Evans, III, Oak Ridge, TN (US)

(73) Assignee: UT-Battelle, LLC, Oakridge, TN (US)

( * ) Notice: Subject to any disclaimer, the term of this patent is extended or adjusted under 35 U.S.C. 154(b) by 491 days.

(21) Appl. No.: 12/729,671

(22) Filed: Mar. 23, 2010

(65) Prior Publication Data
US 2010/0241241 A1  Sep. 23, 2010

Related U.S. Application Data

(60) Provisional application No. 61/162,614, filed on Mar. 23, 2009.

(51) Int. Cl.
*A61F 2/04* (2013.01)
*A61F 2/48* (2006.01)
*A61M 5/00* (2006.01)

(52) U.S. Cl.
USPC ............... 623/23.68; 623/23.67; 623/23.7; 623/23.71; 623/24; 604/8; 604/9

(58) Field of Classification Search
USPC ........... 623/1.24–1.26, 2.1–2.42, 23.64–23.7, 623/24, 25
See application file for complete search history.

(56) References Cited

U.S. PATENT DOCUMENTS

| | | | |
|---|---|---|---|
| 5,300,020 A * | 4/1994 | L'Esperance, Jr. | 604/9 |
| 6,283,959 B1 | 9/2001 | Lalonde et al. | |
| 7,699,882 B2 * | 4/2010 | Stamper et al. | 623/1.11 |
| 2004/0254625 A1 | 12/2004 | Stephens et al. | |
| 2005/0240147 A1 | 10/2005 | Makower et al. | |
| 2007/0142907 A1 | 6/2007 | Moaddeb et al. | |

OTHER PUBLICATIONS

International Search Report dated Dec. 23, 2010.
Harrison et al., Fetoscopic Temporary Tracheal Occlusion for Congenital Diaphragmatic Hernia: Preclude to a Randomized, Controlled Trial, Journal of Pediatric Surgery, Jul. 2003, vol. 38, No. 7, at pp. 1012-1020.

* cited by examiner

*Primary Examiner* — David Isabella
*Assistant Examiner* — Yashita Sharma
(74) *Attorney, Agent, or Firm* — Scully, Scott, Murphy & Presser, P.C.

(57) ABSTRACT

Valve implant systems positionable within a flow passage, the systems having an inlet, an outlet, and a remotely activatable valve between the inlet and outlet, with the valves being operable to provide intermittent occlusion of the flow path. A remote field is applied to provide thermal or magnetic activation of the valves.

10 Claims, 13 Drawing Sheets

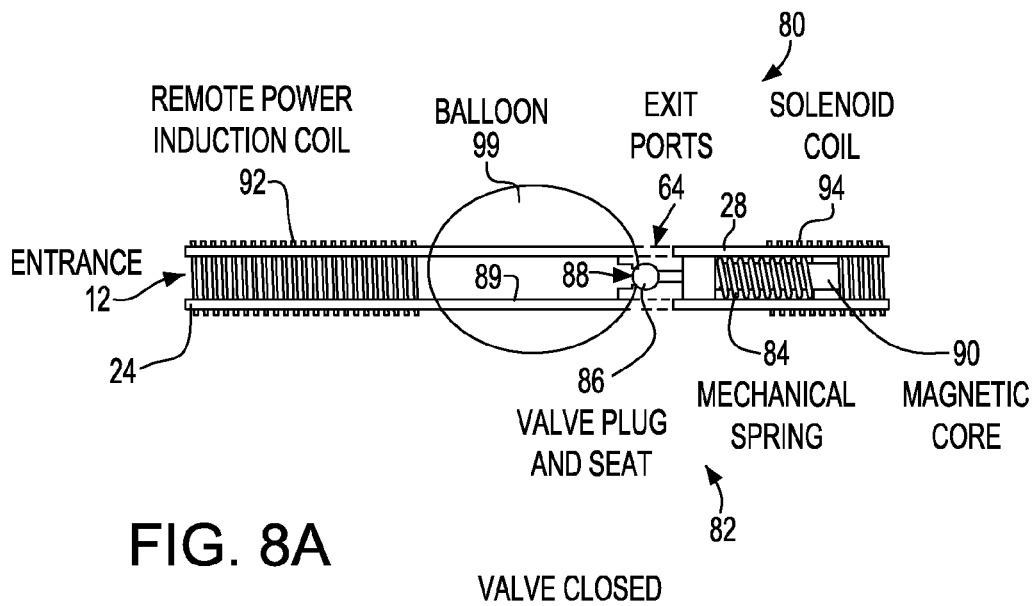
FIG. 8A  VALVE CLOSED
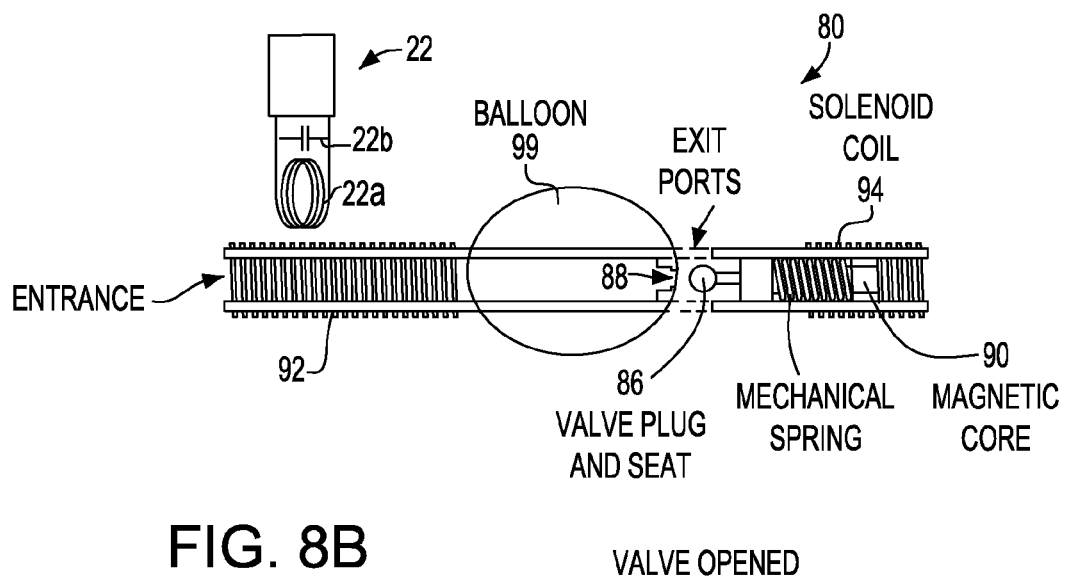
FIG. 8B  VALVE OPENED

INFLATION OCCURS WHILE VALVE IS
CLOSED THROUGH AN OUTER LUMEN

LATCHING MECHANISM CAUSES VALVE BODY TO ROTATE AS THE VALVE OPENS.

VALVE LATCHING MECHANISM CAUSES BODY TO ROTATE INTO A SLOT THAT HOLDS THE VALVE OPEN UNTIL NEXT ACTUATION CAUSES IT TO ROTATE TO CLOSED POSITION.

REMOTE ACTUATED VALVE IMPLANT

CROSS REFERENCE TO RELATED APPLICATION

This application claims the benefit of priority under 35 U.S.C. §119(e) of U.S. Provisional Application No. 61/162,614, filed on Mar. 23, 2009.

GOVERNMENT RIGHTS

This invention was made with government support under Contract No. DE-AC05-00OR22725 awarded by the U.S. Department of Energy. The government has certain rights in the invention.

FIELD OF THE INVENTION

The present disclosure relates to the field of implantable medical devices. More particularly, the disclosure relates to a system that enables a valve to be inserted within the body and remotely activated for controlling the flow of fluid in physiological channels.

BACKGROUND OF THE INVENTION

A medical condition known as congenital diaphragmatic hernia (CDH) is a potentially fatal congenital birth defect in fetuses characterized by abnormal development of the diaphragm which causes herniation of abdominal organs in the chest, resulting in decreased lung development in the fetus. CDH is one of the leading causes of in-hospital neonatal death.

One technique used to treat CDH is a balloon tracheal occlusion procedure such as described in JOURNAL OF PEDRIATRIC SURGERY, Vol. 38, No. 7 (July 2003) at pp. 1012-1020. In accordance with the balloon tracheal occlusion (TO) procedure, under direct visualization, a detachable balloon is positioned just above the fetal carina and inflated with an isotonic solution to provide an occlusion or obstruction. The inflated balloon is left in place until either the fetus is delivered or a removal procedure is performed when the fetus is approximately 34 weeks of age. While the TO procedure has provided some benefits, various disadvantages are believed to be associated with the procedure.

SUMMARY OF THE INVENTION

The disclosure relates to a valve implant system positionable within a flow passage, the system comprising an inlet, an outlet, and a thermally activatable valve between the inlet and outlet. The system may be located in a flow path and used to provide intermittent occlusion of the flow path.

The valve may be provided by a tubing or other conduit having therein a polymer that changes phase upon application of heat. The phase-change of the polymer results in the polymer occluding flow through the valve. At ambient temperature (e.g. body temperature) the polymer expands and blocks flow. When heated, the polymer changes phase, shrinks, and permits flow. The polymer may also be engineered to reverse the temperature control characteristics. That is, to have the valve in an open state under ambient conditions and to occlude flow through the valve when heated.

The valve system may be located in a flow path and used to provide intermittent occlusion of the flow path. For example, the system may be used to treat CDH by using the valve system to intermittently occlude the fetal trachea. However, the system is suitable for additional uses within the body for controlling fluid flow.

In accordance with a particular embodiment, a valve implant system is configured for being disposed within a flow passage and includes a left end tube connected to a left intermediate tube, which in turn is connected to a balloon having a diameter sized to be positioned within and blocking a flow passage. A valve tube is disposed in the balloon and is connected to the left intermediate tube, and a polymer is disposed in the valve tube. The polymer is selected to expand at ambient temperature and shrink when heated above ambient temperature, and the polymer is configured and disposed for blocking the passageway of the valve tube at ambient temperatures and for shrinking when the polymer is heated to open the passageway in the valve tube.

A heater is disposed proximate the polymer for heating the polymer; and a power supply provides power to the heater to cause the heater to heat the polymer and open the passageway in the valve tube. One end of a right intermediate tube is connected to the balloon and the valve tube at the second end of the valve tube; and a right end tube is disposed on the other end of the right intermediate tube. In this configuration, when the polymer is heated, an open composite passageway is formed through the left and right end tubes, the left and right intermediate tubes and the valve. When the polymer is unheated and attains ambient temperature the polymer expands and the composite passageway is blocked by the polymer.

Herein the terms "left" and "right" or "first" and "second" are used as proper names to help distinguish one part from another, but no position information is intended. In other words, a right structure or thing may be positioned anywhere, including on the left, and a first structure or thing is not ordered in any sense with respect to a second structure or thing.

The system may also include side ports formed in the sides of the left and right intermediate tubes for allowing fluid flow between the passageways and the exteriors of the left and right intermediate tubes. Also, a MEMS diaphragm pressure transducer may be mounted to sense the pressure in the composite passageway, and a communication link may be provided for transmitting information corresponding to the pressure sensed by the pressure transducer. The pressure measurements may be used in conjunction with valve parameters to compute flow rates as a type of flow sensor. Other flow sensors including thermal mass flow meters or "hot-wire" anemometers may be used in conjunction with this device. Likewise temperature sensors may be mounted to sense the temperature of the heater or polymer, and a communication link may transmit information corresponding to the temperature sensed by the temperature transducer. The system may also include a power transmitter, such as an RF transmitter, for transmitting power to the power source, and the power source may be a receiver of electromagnetic energy, such as a coil. 12.

In yet further embodiments, electromagnetic valves are provided which include an energy receiving coil and an actuation coil. The valves are normally in a "closed" state to restrict fluid from traveling from the inlet through the valve and out the outlet. The valves are placed in an "open" state by applying an external electrical field to the energy receiving coil to activate the actuation coil to place the valve in an "open" state. The valves may be configured to return to a "closed" state upon removal of the field, or to remain "open" if desired.

In further embodiments, means are provided for locking the electromagnetic valve open to allow for the procedure to be discontinued at the desired lung growth and as a means to open air passageways post delivery.

Further means are provided for remotely "deflating" the balloon which positions the occlusion device in the trachea in which case it would be naturally expirated prior to birth negating the need for a removal procedure. Means for deflating the balloon include using the thermally activated polymer as a means to seal the balloon itself. Alternately, this could be accomplished with an electromagnetic valve configuration. The remote valve deflation using thermally sensitive polymers may be incorporated with remote fluid control valve using resonant circuits that are tuned to different frequencies.

In another embodiment, a thermally activated valve having an internalized heating element and a thermally responsive polymer grafted thereon is provided. The thermally activated valve also has an outer bore tubing within which the internalized heating element and thermally responsive polymer is arranged.

In another embodiment, a thermally actuated valve having a valve element including a thermally responsive polymer and a solid element attached to the thermally responsive polymer is provided. The valve element switches between at least two configurations to adjust the flow rate of fluid through a valve seat.

In another embodiment, a thermally actuated valve is provided with a copolymer formulation allowing the valve to be in either a normally closed state or a normally open state.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein:

FIGS. 8A and 8B show an alternate embodiment of an implant valve system having an electromagnetic valve.

DETAILED DESCRIPTION

Referring to FIGS. 1, 1A, 2A, and 2B, one embodiment of a remote actuated valve implant system 10 is shown. The system 10 may be used in medical procedures involving the control of fluid flow in physiological channels. The system 10 may be used to treat medical conditions such as CDH, hydrocephalus, urinary incontinence, diabetes, gall bladder disease, and diseases of the reproductive system.

Figure 1:
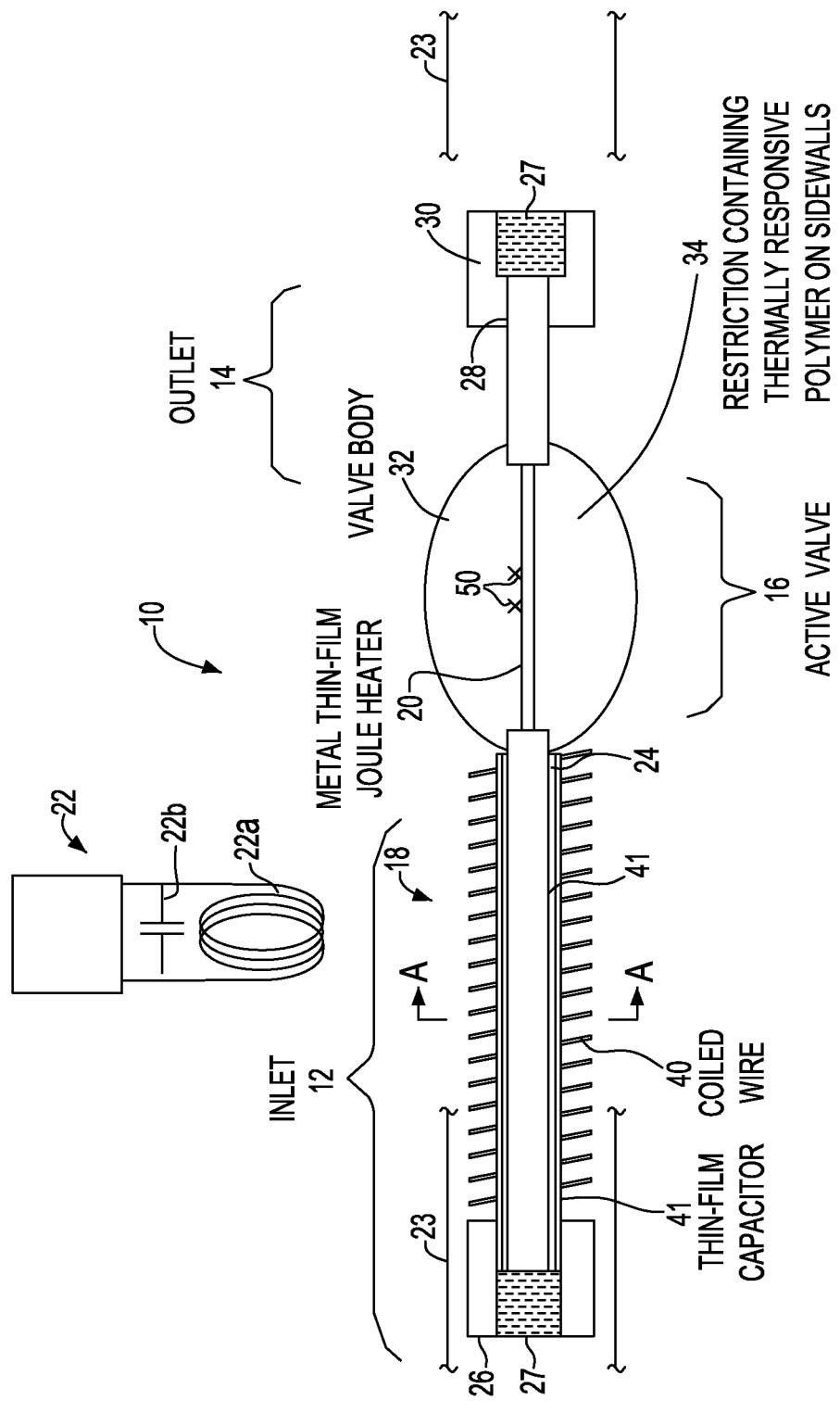
FIG. 1 shows a remote actuated valve implant system according to one embodiment of the disclosure configured for use in treating CDH.

As illustrated in FIG. 1, the system 10 includes an inlet 12, an outlet 14, a thermally activatable valve 16, an electrical circuit provided by a pickup coil 18 electrically coupled to a heater 20, and an external electrical power source 22.

Figure 2A:
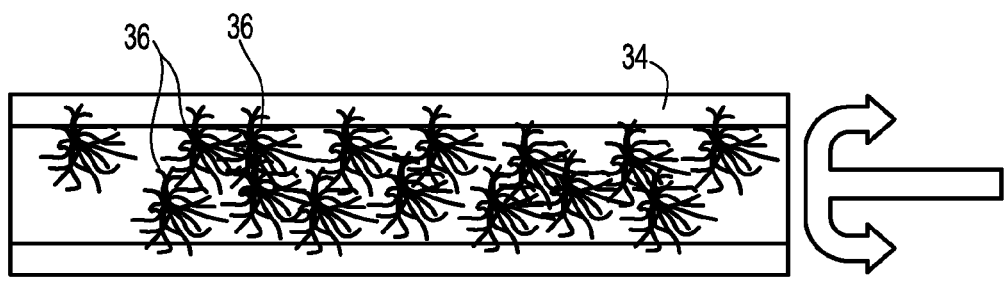
FIGS. 2A and 2B show polymer within tubing as utilized in the system of FIG. 1.
Figure 2B:
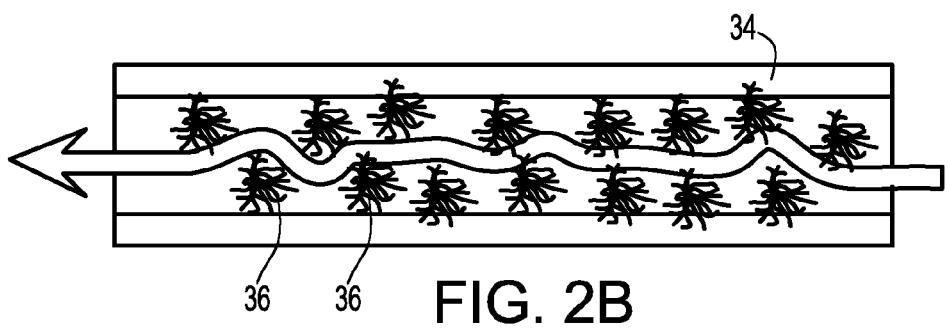

A basic operation of valve 16 is illustrated in FIGS. 2A and 2B. The valve 16 is normally in a "closed" state to restrict fluid from traveling from the inlet 12 through the valve 16 and out the outlet 14. The valve 16 is placed in an "open" state by applying an external field with the power source 22 to the pickup coil 18 to power the heater 20 to heat and thereby activate the valve 16 to the "open" state. As used herein "field" is used broadly to include an electric field, magnetic field or electromagnetic wave. Upon removal of the field of power source 22, the valve 16 will return to the "closed" state. Thus, the system 10 may be located in a flow path 23 and used to provide intermittent occlusion of the flow path 23.

As an example, the system 10 described herein is configured for use in treating CDH. In this regard, the inlet 12 may be provided by tubing 24, such as 800 micron o.d., 300 micron i.d. medical grade tubing, such as polymide-coated, fused-silica capillary tubing. The free end of the tubing 24 can include a section of 1-mm o.d., 800 micron o.d. silicone tubing 26. The tubing 26 may be useful to reduce the potential of tissue interactions at the possibly sharp, cleaved end of the tubing 24. In addition, or in the alternative, a screen or filter material 27 may be provided to filter any undesirably large particles.

The outlet 14 can be substantially identical to the inlet 12, and includes tubing 28, made of the same material as the tubing 24. The free end of the tubing 28 can include a section of 1-mm o.d., 800 micron i.d. silicone tubing 30 or the filter 27 or both.

The thermally activatable valve 16 includes a valve body 32 surrounding a section of tubing 34 and enclosing a thermally responsive polymer 36. The polymer 36 is expanded under ambient body conditions (e.g. body temperature) and effectively restricts fluid flow through the tubing 34. Thermal activation of the polymer 36 shrinks or reduces the volume of the polymer 36 so as to enable fluid to flow through the tubing 34, and in one embodiment the polymer may shrink to 50% of its original volume.

The valve body 32 functions to immobilize the valve 16 within the desired fluid passageway 23, such as the fetal trachea, and also functions to thermally insulate the thermally responsive polymer 36 within the tubing 34 from surrounding body tissue. In this regard, further insulation may be provided by providing a secondary layer of insulating material or by filling the valve body with a gas or other insulating material. As described herein, in one embodiment, the valve body 32 may be provided as by a pediatric inflatable balloon of the type used in a tracheal occlusion procedure. However, it will be understood that other structures effective to immobilize the valve 16 within the fluid passageway 23 may be used.

The ends of the tubing 34 are connected to the tubing 24 and 28 of the inlet 12 and outlet 14, respectively. The tubing 34 is smaller than the tubing 24 and 28 of the inlet 12 and outlet 14, and can, for example, be 300 micron o.d., 75-150 micron i.d. medical grade tubing, such as polymide-coated, fused-silica capillary tubing.

The thermally responsive polymer 36 is prepared so as to exist in a swollen state at normal body temperature (e.g. ~37-39° C.), and to collapse at an elevated temperature close to but above normal body temperature (e.g. ~40-41° C.). For the polymer 36 to be suitably thermally responsive, the polymer 36 preferably has a lower critical solution temperature (LCST) slightly above physiological temperature, such as 40-41° C., so that the polymer undergoes a phase change at the LCST temperature. In this regard, the terminology "phase" or "phase change" as used herein refers to changes in the molecule shape and swelling, including changes in the hydrophobic or hydrophilic characteristics. For example, the phase change of the polymer 36 in the tubing 34 causes the polymer to contract and renders the valve 16 in an open state enabling fluid to flow through the tubing 34.

The polymer 36 is preferably provided within the tubing 34, such as by covalent attachment of either discrete spheroids of the polymer (packed bed), or by in-situ polymerization of the polymer using conventional acrylamide to silica adhesion techniques (continuous monolith).

For example, with reference to FIGS. 2A and 2B, there is shown the polymer 36 within the tubing 34, with the tubing 34 being provided by a single channel of 150 micron o.d., 75 micron i.d. fused silica. The internal wall of tubing 34 is coated using 3-methaacryloxypropytrimethoxysilane (MAPTOS) to bind polyacrylamide based hydrogel during radical polymerization. This molecule will chemically bind or anchor the polymer on the internal wall of the tubing 34. Exemplary polymers include, but are not limited to, a polymer such as pNIPAM copolymered with N,N-dimethylacrylamide (DMAA) or other suitable copolymer material adjusted to provide an LCST of 40° C. or more. At body temperature, the polymer 36 will exist as a hydrogel and spatially occlude the flowpath 23, as seen in FIG. 2A, generating backpressure. At temperatures above the LCST, as will occur upon application of the external electrical field of power source 22, the polymer 36 will collapse against the sidewall (monolith), as seen in FIG. 2B, and allow fluid flow. Backpressure is dependent on monolith porosity and polymer filling monolith voids. Utilizing parallel paths of smaller diameter will provide higher backpressures when the valve is closed at body temperature. In this regard, multiple parallel capillaries may be used instead of a single tubing element. However, such multiple parallel capillaries will be smaller diameter capillaries, and a filter (such as the filter 27) can be incorporated to filter particles larger than the internal diameter of the entry/exit regions.

Figure 3:
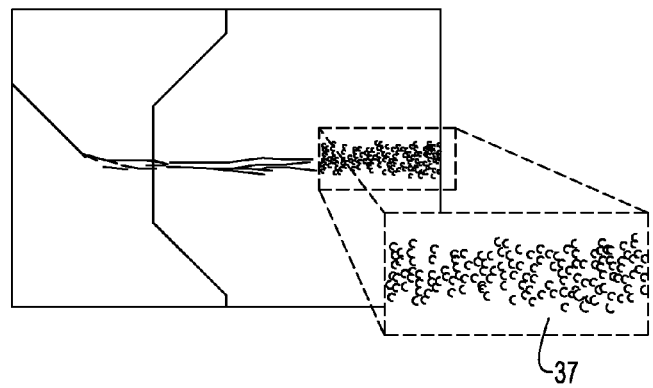
FIG. 3 shows a system for producing thermally-responsive beads for use in the system of FIG. 1.

The polymer 36 may preferably be a hydrogel, such as optimized poly-n-isopropylacrylamide-polyacrylic-acid p(NIPAAm) copolymers, p(NIPAm)-co-DMAA. The monodispersed microgels of P(NIPAAm) and related thermally responsive polymers may be generated using redox initiated polymerization in monodisperse aqueous-in-paraffin emulsion on a microfluidic channel. Generation of microgels using redox initiated polymerization advantageously enables rapid determination and optimization of the LCST and of the swelling volumes of various polymers via evaluation of bead diameter in artificial amniotic fluid with optical microscopy on a heated stage, such as illustrated in FIG. 3, which shows ~20 micron alginate microgels 37. Preferably, when the polymer 36 is heated, it shrinks and provides a passageway having a diameter of about 30 to 100 microns in the tubing 34. The open passageway will typically have an irregular shape and a circuitous path, and reference to a diameter of such irregular passageway refers to a diameter in a round tube that would provide the same flow as the irregular passageway. Such diameter may be considered an effective diameter.

Figure 1A:
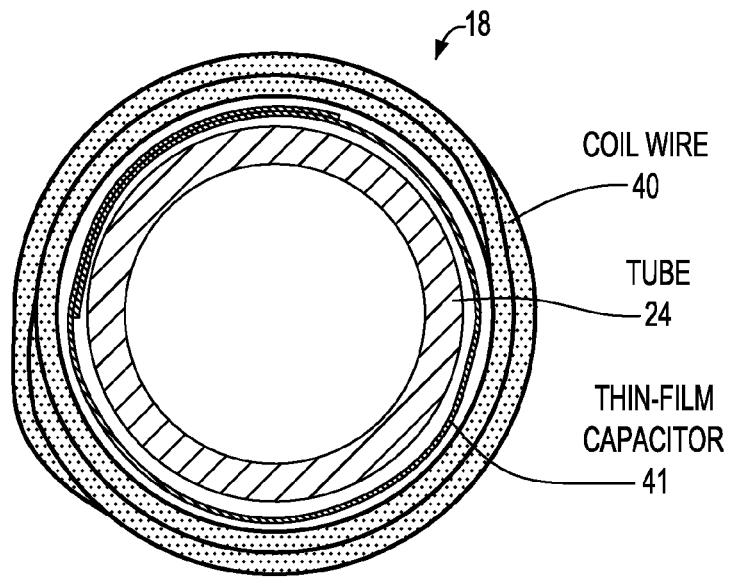
FIG. 1A is a cross-sectional view taken along line A-A of FIG. 1.

As illustrated in FIG. 1A, the pickup coil 18 may be provided, for example, by wrapping a coil wire 40 around the tubing 24, or the tubing 28, or both. The coil 18 may be configured to operate in either series or parallel resonance mode by the addition of a capacitor. The wire 40 may be 50+ gauge wire suitable for making a magnet. The wrapped wire 40 constructs the coil 18 which may be excited by application of the external field of power source 22 which may be provided by an external coil 22a or an electrical transmitter such as a radio transmitter. The wire 40 is electrically connected to the heater 20 such that when the external electrical field of source 22 is brought in proximity to the wire 40, a current is induced in the wire 40 to power the heater 20.

The power source 22 may be provided as by an externally located drive coil 22a capable of generating a sufficient field to induce a desired voltage on the pickup coil 18 sufficient to provide the desired power to the heater 20. The power source 22 may also incorporate a capacitor 22b to operate in series or parallel resonance mode thus improving efficiency of oscillation and frequency selectivity. For example, 60 µW of thermal power for a period of about 60 seconds may be achieved by energizing a coil made of 52 gauge wire having about 200 turns with 1 mm o.d. using an RF field centered in one of the Industrial, Scientific, and Medical (ISM) bands (6.78 MHz, 13.56 MHz, 27.12 MHZ, or 40.68 MHz) or other suitable band.

A flexible-film capacitor 41 which can conform to the hollow, tubular geometry may be included with the wire 40 to tune the resonance of the circuit provided by the pickup coil 18. That is, the wire 40, capacitor 41, and the resistance of the heater 20 are selected to resonate with the inductive drive coil 22a and capacitor 22b. The capacitor 41 may also be constructed using other conventional methods. In addition, ultrasound imaging may be used to facilitate alignment of the power source 22 with the pickup coil 18. Alternatively, the power source 22 may be provided partly or in whole by use of an implanted battery as opposed to being remote.

The heater 20 may in one embodiment be provided as by patterning the tubing 34 with a physical vapor deposited thin-film metal resistance heater using shadow masking with laser machined polyimide-based adhesive templates. In another embodiment, shown in FIG. 4 installed within a fetal trachea, a resistive wire 25 may be wrapped around the tubing 34 to provide the heater 20. The heater 20 is operable to heat the polymer 36 within the tubing 34 up to the desired temperature to accomplish phase change. To avoid overheating, the heater 20 is configured so as to not raise the temperature of the polymer 36 more than about 5° C. The exterior of the overall assembly of the inlet 12, outlet 14, valve 16, and heater 20 is preferably passivated or insulated by a conformal coating of a passivating or insulating material, such as Parylene-C.

Modified examples of the above-described system 10 is provided below.

In a first modification, conductive materials may be placed within, around, and/or enmeshed in the polymer 36. Passage of DC or AC current through the conductive materials release heat, thereby raising the temperature of the conductive materials and the polymer 36. The valve 16 is thereby actuated by Joule heating.

In a second modification, valve 16 can be actuated by induction heating. Conductive material may be placed in thermal contact with the polymer 36. The conductive material is heated by electromagnetic induction, where eddy currents are generated within the conductive material and resistance leads to Joule heating of the conductive material.

The conductive material may be a continuous conductive material internal or external to the polymer 36, or the conductive material may be discontinuous conductive materials embedded within or around the polymer 36 such as discrete nano- and microspheres of metals or metallic conductors.

Magnetic materials may be incorporated within, around, or enmeshed in the polymer 36 to provide heating via induction heating. These magnetic materials may include nano- and microparticles of magnetic materials which are heated by inductive heating. These magnetic materials may include Curie thermoregulated materials such that heating can be controlled by the transition of these magnetic materials from ferro/feri magnetic below the Curie point to paramagnetic above the Curie temperature.

In a third modification, the valve 16 can be actuated by ultrasonic excitation. Ultrasonic energy is focused on or around the valve 16 to generate heat in the tissue surrounding, or the materials including and surrounding the valve 16.

As an example, enhanced heating can be achieved by arranging ultrasound contrast agents around the polymer 36 such that the absorption of ultrasonic energy is enhanced in the region surrounding the polymer 36.

In a fourth modification, the valve 16 can be actuated by infrared or near-infrared heating. In particular, near-infrared heating may be beneficial due to the significant tissue penetration depth of near infrared at wavelengths within a therapeutic window of 700-1200 nm.

As an example of near-infrared heating, gold nanospheres are incorporated into the polymer 36. These gold nanospheres may then be heated by near infrared energy, including multiphoton excitation of multiple convergent rays of near infrared radiation.

In a fifth modification, the valve 16 can be actuated by physiological situations. Examples of physiological situations that can be harnessed to actuate valve 16 include, but are not limited to, elevated body temperatures due to fever, infection, microbial process, increased activity/metabolism of cells and tissue including exercise and physical exertion, and increased growth/proliferation/metabolism of cells, including tumor cells.

In a sixth modification, the valve 16 can be actuated by convective or conductive heating of the tissue surrounding the valve 16.

Figure 13:
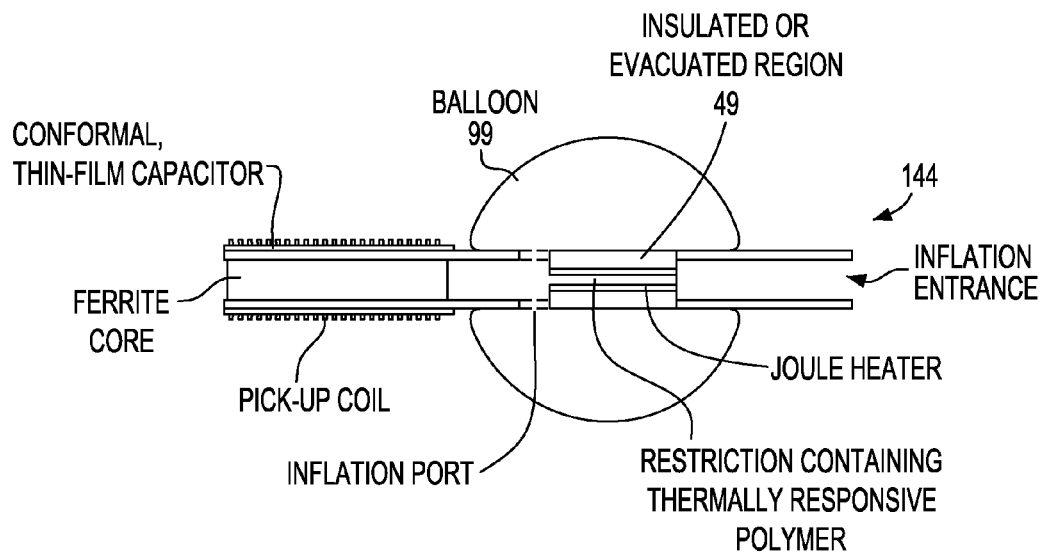

An insulating layer may also be provided around the heater 20 to reduce energy requirements. An example of an insulating layer 49 arranged around the heater is shown in FIG. 13. The system 10 may also utilize a thermostat system in conjunction with the heater 20 to inhibit temperature increases of the system 10 beyond desired operation levels. For example, the system 10 may also include a cut-off switch, such as may be provided by a bi-metallic strip of material which will terminate power to the heater 20 at a desired temperature. Alternatively, thermocouples 50 or thermistors or the like may be located on the tubing 34 to measure the temperature and incorporate that measurement into an algorithm for supplying power to the heater 20 to control temperature. Furthermore, integrated pressure measuring devices may be used with implanted signal processing to fully automate control of the valve 16, enabling optimized pressure-based valve control.

Figure 4:
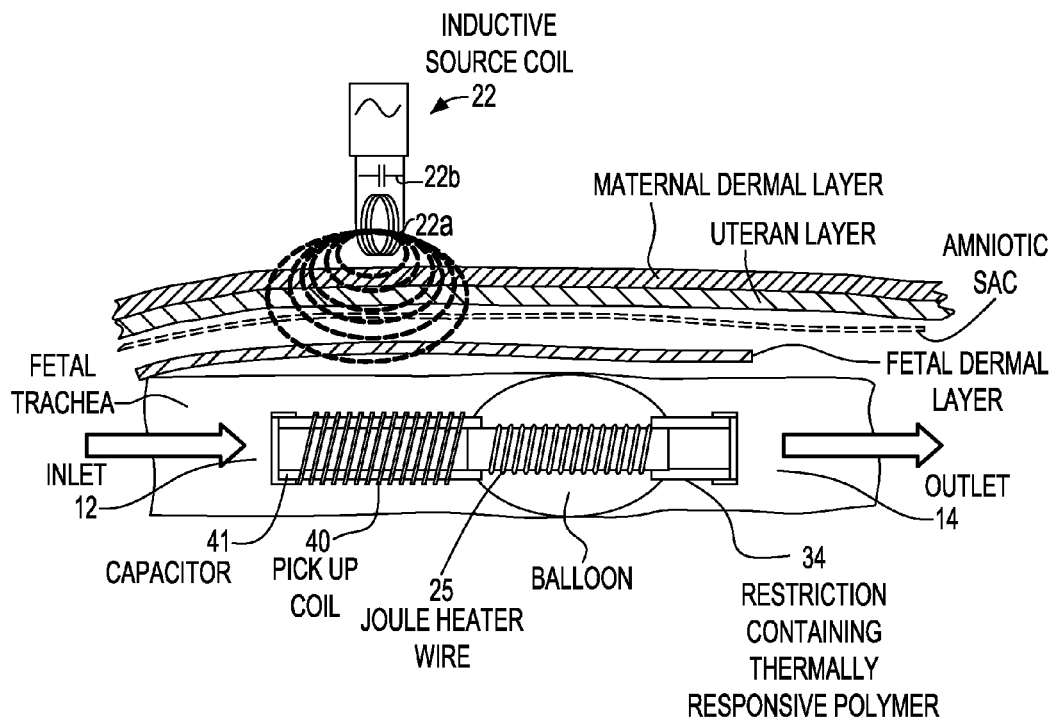
FIG. 4 shows an alternate embodiment of a heater for use with the system of FIG. 1.

In use, an assembly having the inlet 12, outlet 14, valve 16, coil 18, and heater 20 is desirably located in a physiological channel of the body, such as a fetal trachea as shown in FIG. 4. As desired, the power source 22 may be utilized to place the valve 16 in a closed state as described to control the flow of fluid through the valve, and hence the physiological channel of the body. Thus, in the case of treating CDH, the fetal trachea may be intermittently occluded, versus continuously occluded as occurs with conventional TO techniques. It is believed that treatment advantages may be achieved by providing intermittent occlusion.

Figure 5A:
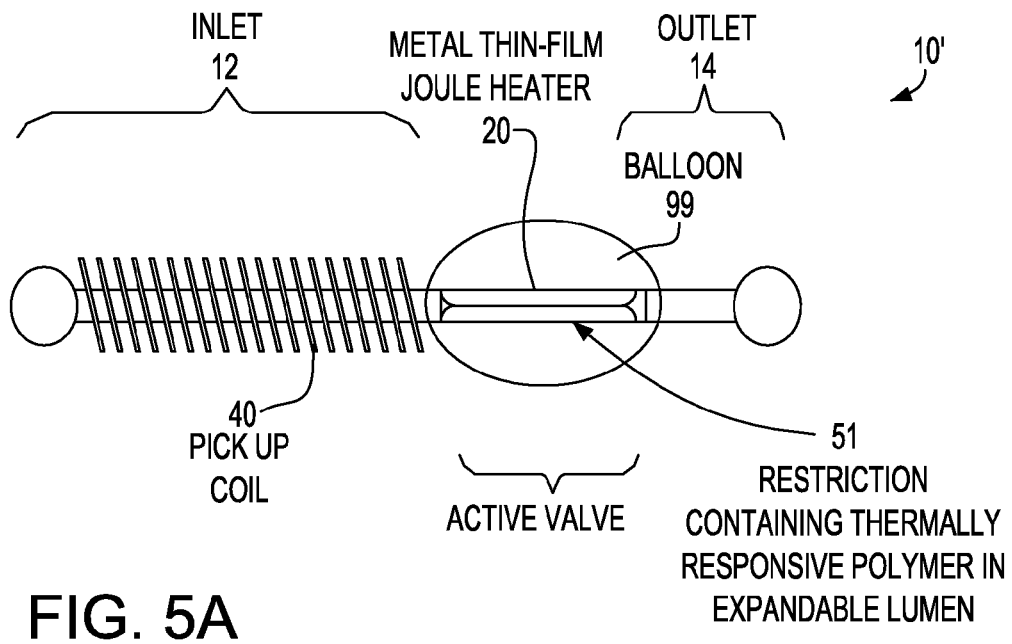
FIGS. 5A and 5B show an alternate embodiment of the system of FIG. 1, in which the polymer is contained within expandable lumens.
Figure 5B:
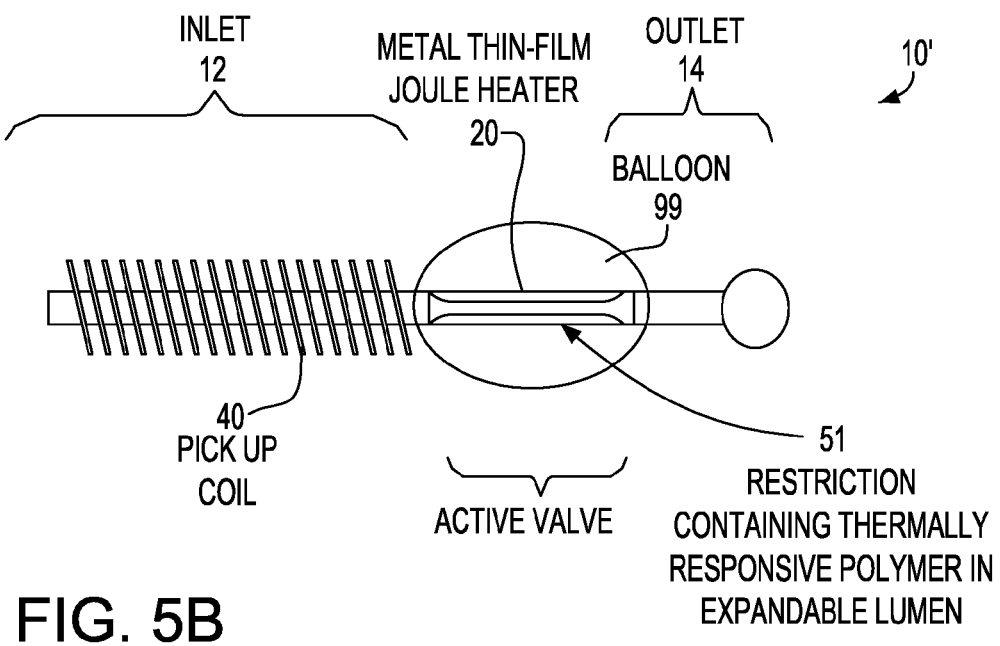

With reference to FIGS. 5A and 5B, there is shown a further embodiment of a system 10' that may be identical to the system 10, except the polymer 36 is contained within expandable lumens 51 within the tubing 34. The lumens 51 are adjacent the sidewall of the tubing 34 such that when the valve is in the normal closed state (FIG. 5A), the swollen polymer expands the lumens 51 to occlude the tubing 34. The lumen provides an elastic capability to allow for expansion and contraction of the polymer. The expandable lumen incorporates a means for allowing water to be expelled or absorbed into this system such as a membrane, perforation, or other method. When the external field of source 22 is supplied and the polymer 36 within the lumens 51 is heated, the polymer shrinks and the lumens 51 deflate to open a flow path, as seen in FIG. 5B.

Figure 6A:
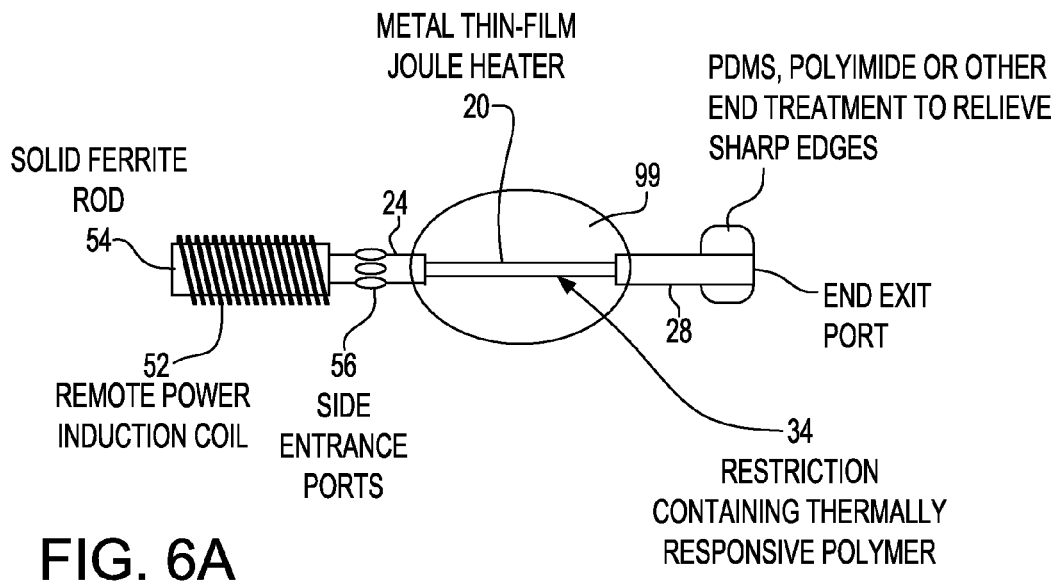
FIGS. 6A and 6B show further embodiments of valve systems incorporating an inductive pickup coil having a ferrite core.

In another embodiment, shown in FIG. 6a, an inductive pickup coil 52 having a ferrite core 54 may be used to provide the coil 18. Such coil/core may be located at the inlet, outlet, or both. The core 54 may be hollow or solid. Since fluid cannot travel through a solid ferrite core 54, side entrance ports 54 are provided in the tubing 24 to provide a fluid entrance in the event a solid core 54 is used. If a coil/core having a solid core were provided on the exit side of the valve, it is understood that exit ports would be provided on the tubing 28 in a similar manner For the purpose of example, the core 54 may be a Type 77 ferrite core, having a length of 10 mm and a 1 mm diameter. The coil 52 is 40 gauge wire (75 micron) of 100 turns wrapped around the core 54.

Figure 6B:
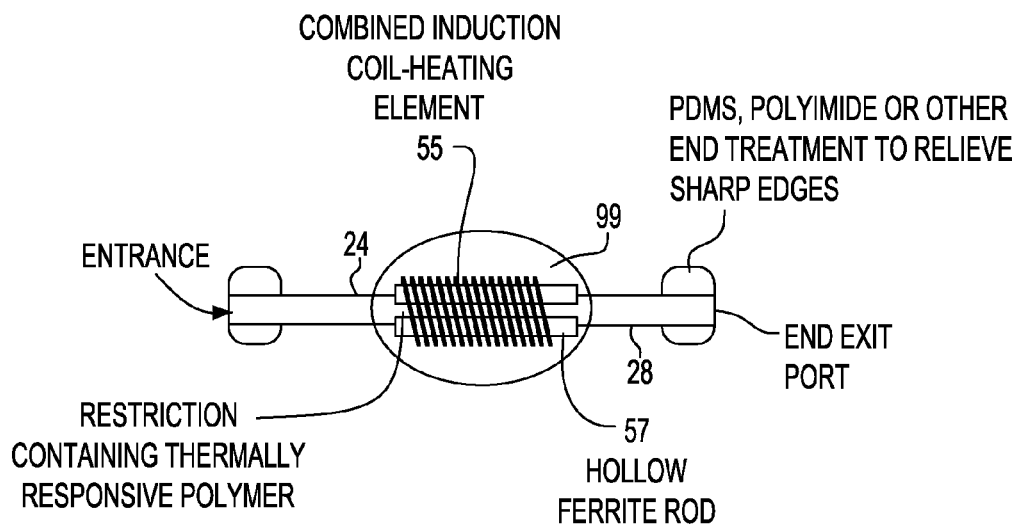

In yet another alternate embodiment, an inductive pickup coil is incorporated into into the heater coil surrounding the thermally responsive polymer to provide a combined induction coil-heating element 55 as shown in FIG. 6b. A hollow ferrite rod 57 may be used to enhance electromagnetic coupling. In this embodiment, the inductive-coil heating element 55 is operated by application of the field of source 22 beyond the self resonant frequency resulting in core heating that can be used for valve actuation.

Figure 7:
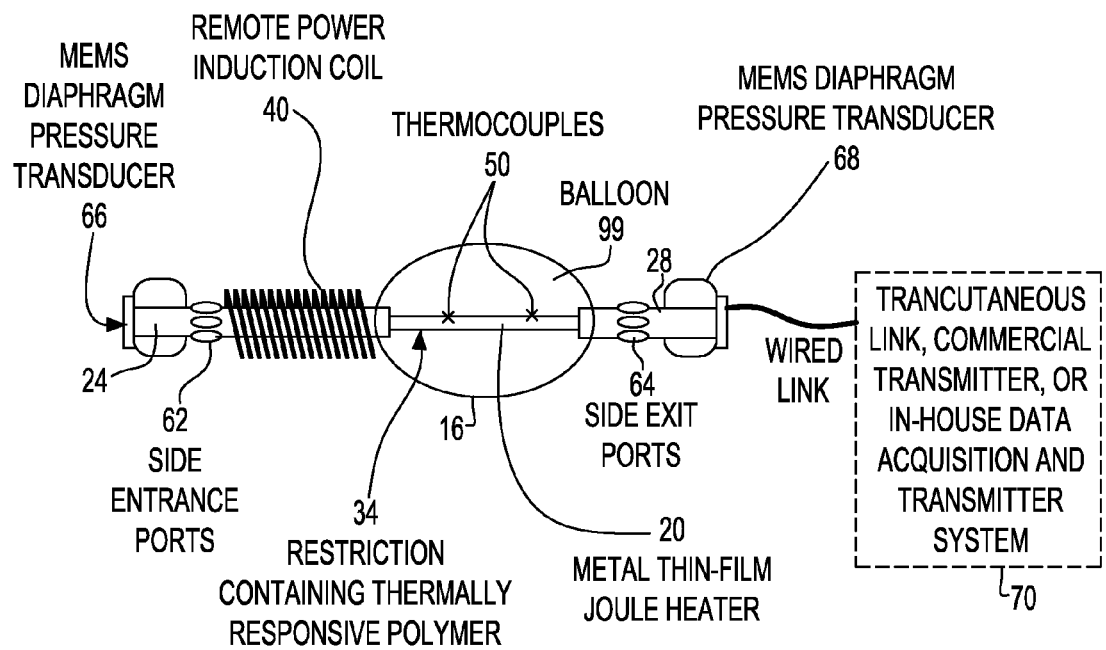
FIG. 7 shows an alternate embodiment of a remote valve implant system configured for use in studying pressure effects of lung development.

With reference to FIG. 7, there is shown yet another alternate embodiment of a system 60 configured to enable remote measurement of the pressure of pulmonary fluids, and to enable control over the release of fluids from the lungs. The system 60 is configured to measure the lung pressure distal to the valve 16 and tracheal pressure proximal to the valve 16. In a preferred embodiment, the system 60 includes the components of the system 10 (bearing like reference numerals) and further includes multiple side inlet ports 62 and exit ports 64 that extend from the interior passageways to the exterior of the tubes 24 and 28 to avoid blockage of flow by the tracheal wall, a pressure transducer 66 located at the inlet, and a pressure transducer 68 located at the outlet, both of which are preferably MEMS diaphragm pressure transducers. An external data link 70, such as a wired link extending from the transducers and thermocouples, is also be included for collecting measured data during operation of the system 60. The data link 70 may also be a wireless transmitter, and whether wired or wireless, it is understood that the various measuring components shown in FIG. 7 are electrically connected to the link 70 by wire or otherwise. The connections are not shown in FIG. 7, or other figures, to improve the visual clarity of the illustration.

The system 60 is configured for allowing the study of CDH in animal models and facilitates the study of correlations between lung pressure, volume, and lung development in the fetal pulmonary environment. The pressure information is relevant to the physiology of lung development, the effects of pressure on lung expansion, and the role of pressure on cell differentiation. Also, based on the pressure differential across the system and the amount of restriction in the valve, the fluid flow rate through the open valve may be evaluated. In addition, temperature measurements provided by the thermocouples enable verification of the valve operation and remote power delivery, as well as maintenance of the temperature of the system within a desired range.

With reference now to FIGS. 8A and 8B, there is shown another embodiment in which a system 80 has an electromagnetic valve 82. This embodiment uses the inductive power transfer system previous described. The valve 82 includes a mechanical spring 84 that urges a plug 86 against a valve seat 88 located on the exit end of a flow conduit 89 associated with the valve 82. The plug 86 is attached to a permanent magnet 90. A remote power induction coil 92 is provided for co-acting with the external field of source 22, with a wire electrically connecting the coil 92 and a solenoid coil 94. The solenoid coil 94 surrounds the spring 84 and magnetic core 90 to provide an electromagnet when powered to retract the plug 86 from the valve seat 88. The valve 82 is normally closed under pressure supplied by the spring, as seen in FIG. 8A. However, application of the external field of source 22 to the coil 92 results in retraction of the plug 86 from the valve seat 88 to open the valve while the field of source 22 is applied to the coil 92, as seen in FIG. 8B. Removal of the electric field will then enable the spring 84 to return the valve 82 to the closed position. Since a permanent magnet is utilized in this embodiment, it may be desired to rectify the received power.

Figure 9A:
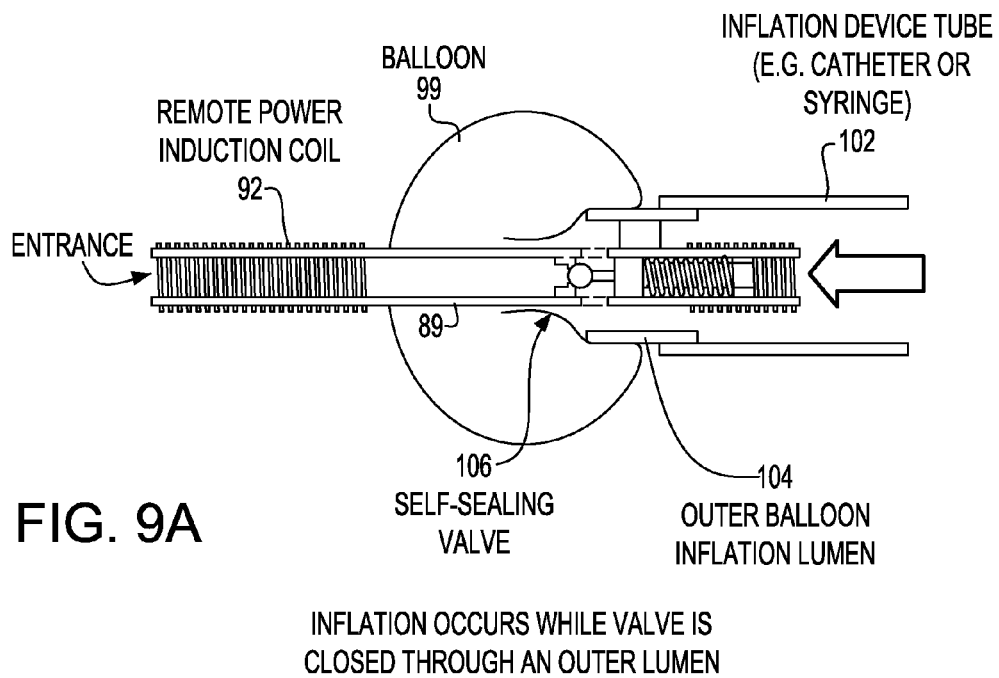
FIGS. 9A and 9B show an inflation device that may be utilized with the systems disclosed herein for inflating a balloon component of the systems.
Figure 9B:
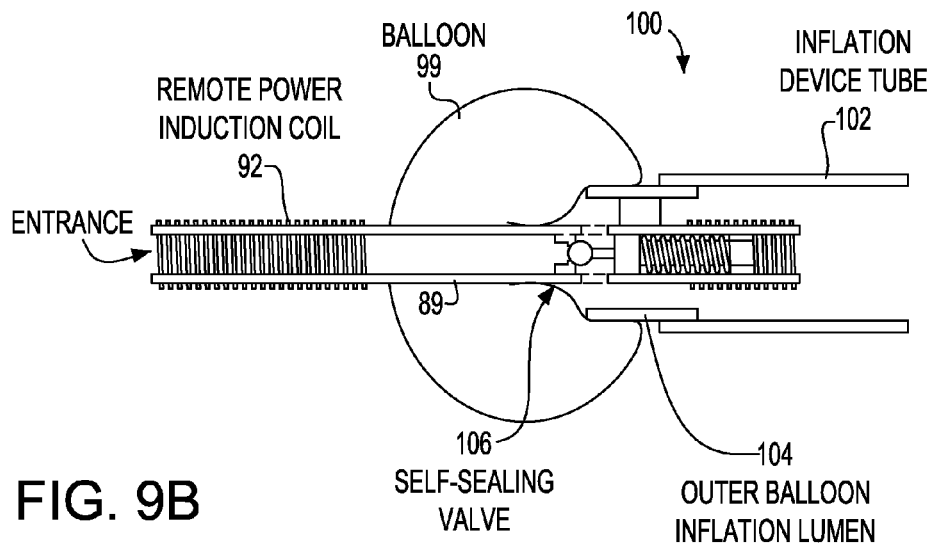

As mentioned previously, the valve body 32 may be provided by an inflatable balloon of the type used in a tracheal occlusion procedure, embolization balloon procedure, balloon angioplasty or stent procedure, or other medical procedure requiring an inflatable balloon. In this regard, and with reference to FIGS. 9A and 9B, there is shown an inflation device 100 that may be utilized in conjunction with the system 80 or the other systems described herein and which facilitates inflation of a balloon 99 which provides the valve body 32. The inflation device 100 includes a tube 102 having a lumen 104 on the end thereof configured for engaging the balloon 99. The balloon 99 is configured to have a self-sealing valve 106 that permits inflation medium to flow from the inflation tube 102 and lumen 104 into the balloon 99 during an inflation step, but which remains in sealing contact with the exterior of the conduit 89 after the balloon 99 is inflated. In this regard, inflation is conducted with the valve 82 in a closed state, such as seen in FIG. 9A. The balloon 99 is shown in a fully inflated state in FIG. 9B, with the valve 106 sealed.

Figure 10A:
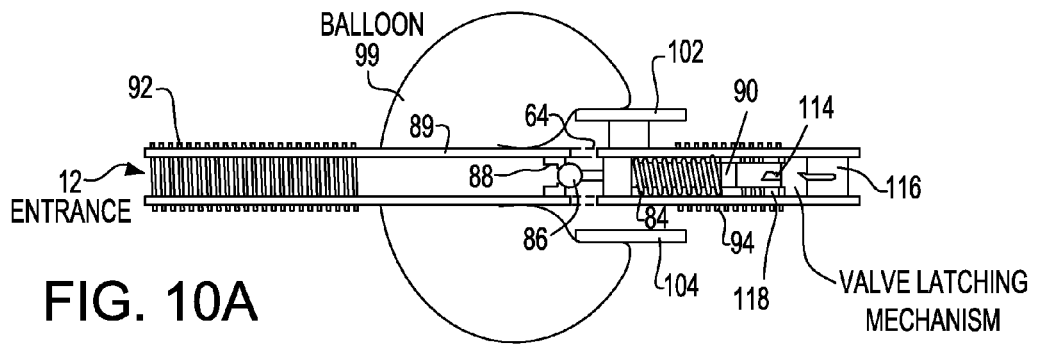
FIGS. 10A-10C show a further embodiment of an implant valve system having a latch mechanism that enables the valve to remain open.
Figure 10B:
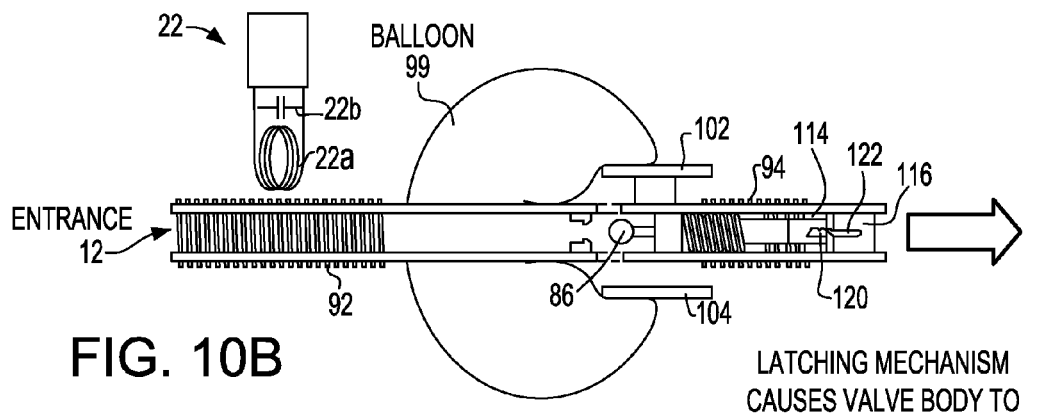
Figure 10C:
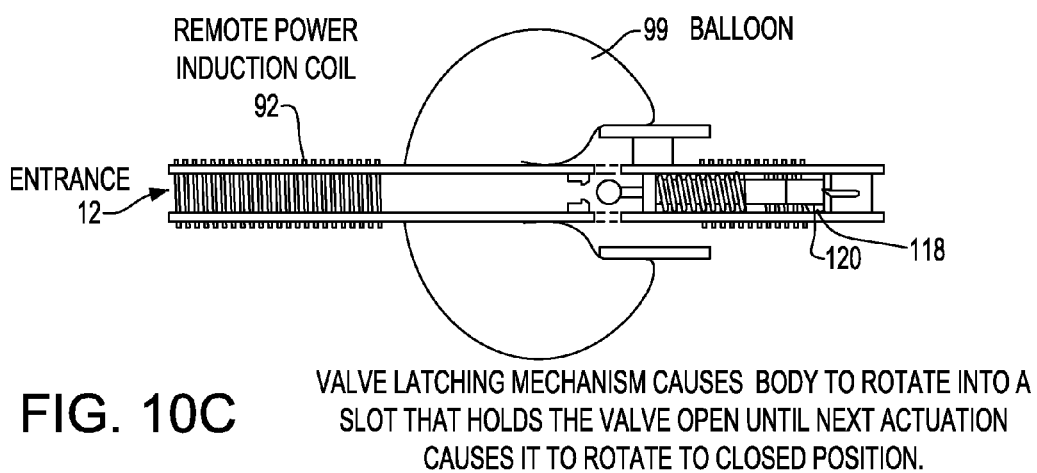

FIGS. 10A, 10B and 10C show a further embodiment of an implant valve system 110 having a latch mechanism 112 that enables the valve to remain open when the electric field is not supplied. The system 110 includes the previously described electromagnetic valve 82 of FIGS. 8A and 8B, and also preferably includes the previously described balloon 99 and inflation device 100 of FIGS. 9A and 9B. The latch mechanism 112 may be a mechanical latch or catch system associated with the moving portions of the valve to maintain them in a desired positional orientation. For example, as shown, the latch mechanism includes a catch 114 connected to the end of the magnetic core 90, a translator 116 within the exit end to contact the catch 114 and cause rotation thereof, and a slot 118 within the exit end to receive the catch 114.

As shown in FIG. 10A, the valve 82 is normally closed under pressure supplied by the spring in the absence of the electrical field being applied to the coil 92. However, as seen in FIG. 10B, application of the external electrical field of source 22 to the coil 92 results in retraction of the plug 86 from the valve seat 88 to open the valve. As will be noted, a protrusion 120 of the catch 114 contacts an extension 122 of the translator 116 to cause the valve body 121 to rotate as the valve opens. When the source 22 is removed or turned off, as seen in FIG. 10C, the spring 84 urges the valve body 121 back toward a closed position. However, due to the rotated position of the valve body 121 from contact of the catch 114 with the translator 116, the protrusion 120 is now positioned to be captured by the slot 118 to prevent closure of the valve, rendering the valve in the captured open state shown in FIG. 10C so that the valve remains open without application of the electric field. To close the valve, the electric field is re-applied and the valve body 121 is again rotated and this rotation frees the protrusion 120 from capture. In other words, the valve body 121 is rotated such that the protrusion 120 is no longer positioned to be captured by the slot 118. Thus, when the electric field of source 22 is removed, the spring 84 urges the valve back to the closed position of FIG. 10A.

Figure 11A:
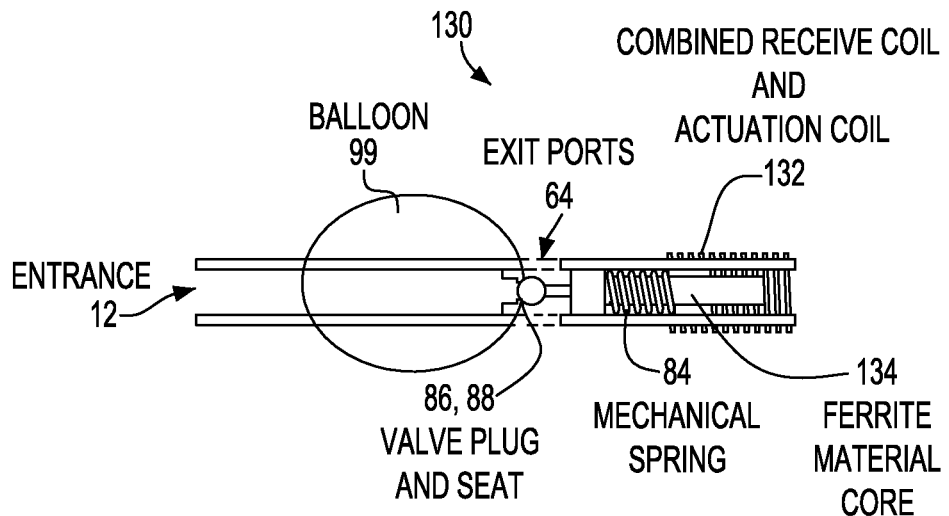
FIGS. 11A and 11B show yet another embodiment of an implant valve system having a combined coil that provides both energy reception and valve actuation functions.
Figure 11B:
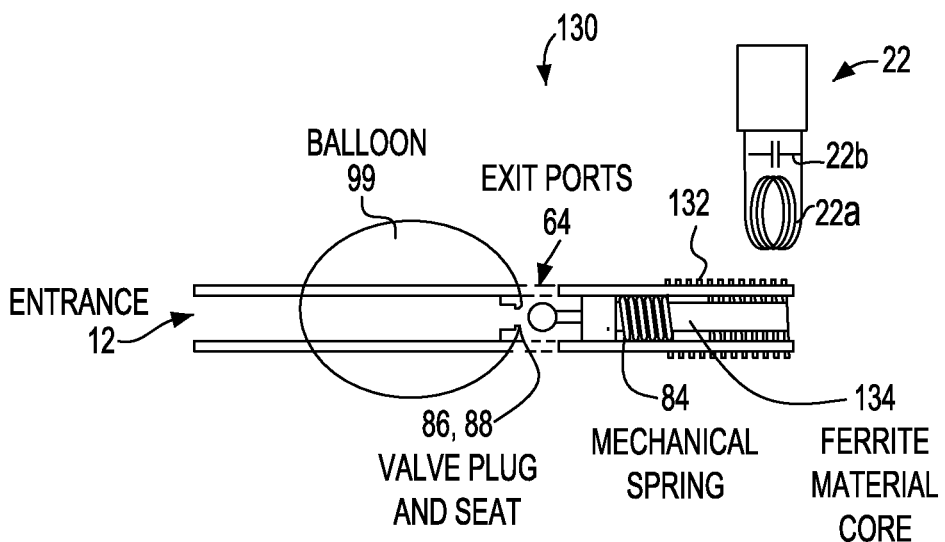

FIGS. 11A and 11B show yet another embodiment of an implant valve system 130 having a combined coil 132 that provides both energy reception and valve actuation functions. The coil 132 is a single coil that provides energy reception from the electric field of source 22 (which applies an RF field) and actuates operation of the valve. The system includes a ferrite material core 134 that is responsive to the source 22. In the absence of the field of source 22, the valve is closed as seen in FIG. 11A. When the coil 132 is activated by the source 22 as seen in FIG. 11B, a current is driven in the coil circuit which produces an RF magnetic field that is uniform near the center of the coil but has a field gradient at both ends. Ferrite material located in these field gradient regions will experience an attractive force, pulling the ferrite core 134 toward the coil 132. With the core 134 positioned asymmetrically within the coil 132 as shown, the core 134 is pulled towards the coil 132. When the pulling force on the core 134 exceeds the force of the spring 84, the valve opens (FIG. 11B).

Figure 12:
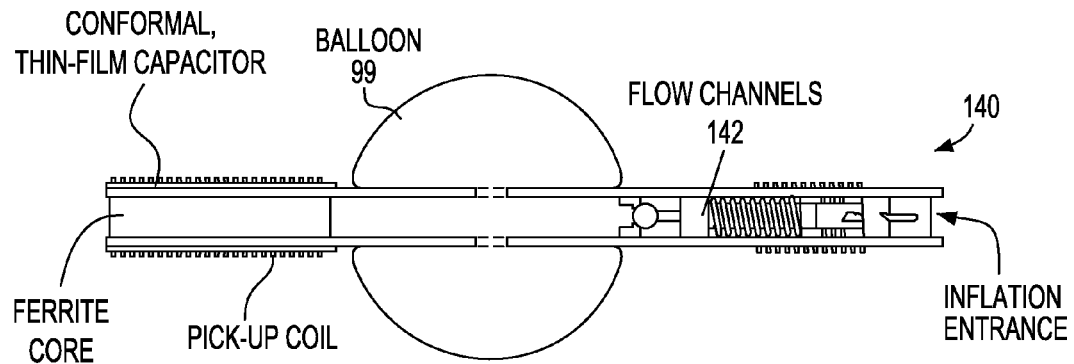
FIGS. 12 and 13 show additional embodiments which facilitate remote deflation of a balloon.

With reference to FIG. 12, there is shown a deflation device 140 which facilitates remote deflation of the balloon 99. For example, as seen in FIG. 12, grooves or other channels 142 are provided for fluid to flow past the valve mechanism. A corresponding thermally activated system 144 is shown in FIG. 13, with the valve shown with an evacuated or otherwise insulating layer around the valve to reduce the amount of energy required to open the valve. The embodiments of FIGS. 12 and 13 are depicted to provide a remotely deflatable balloon structure. These embodiments may be utilized in circumstances wherein the balloon is surgically installed and inflated to occlude flow in a flow passage. Thereafter, the balloon may be remotely deflated to restore flow without the need for surgery. However, it will be understood that these structure may be incorporated with the previously described valve structures as well.

Figure 14:
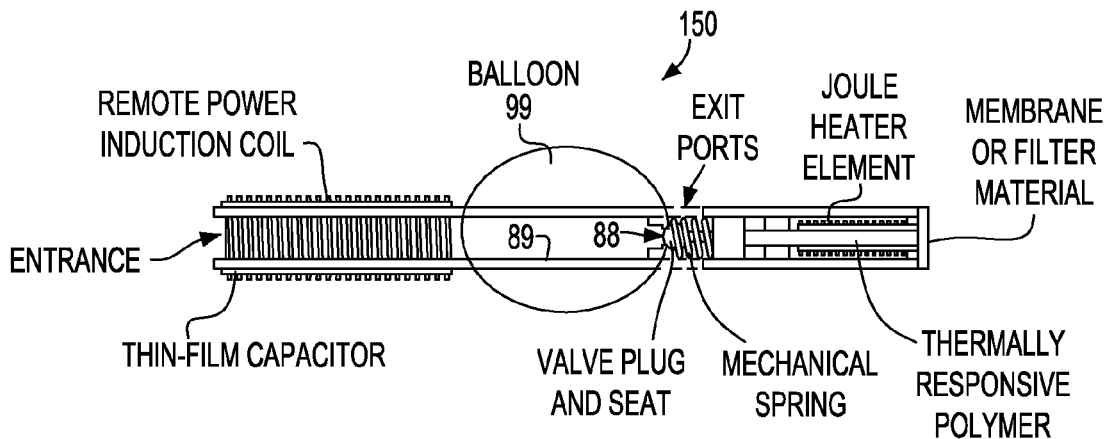
FIG. 14 shows an alternate embodiment of a valve system that utilizes a thermally responsive polymer.

With reference to FIG. 14, there is shown a valve system 150 including a mechanical valve that is similar to the electromagnetically actuated systems described herein. In this embodiment, the valve is actuated by expansion of the thermally responsive polymer or other "smart" material such as shape memory alloy. In the thermally responsive polymer embodiment, the polymer swells at lower temperatures to close the valve. At higher temperatures, the polymer shrinks to open the valve. A membrane is provided to allow the polymer to absorb and exclude fluid.

Figure 15:
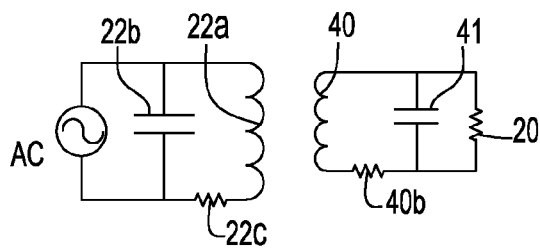
FIG. 15 shows an external electrical power source for the system configured to operate in parallel resonance mode.
Figure 16:
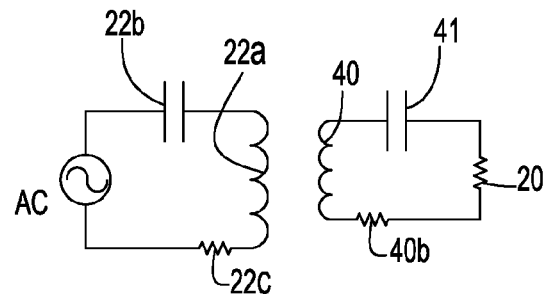
FIG. 16 shows an external electrical power source for the system configured to operate in series resonance mode.

With reference to FIGS. 15 and 16, it will be appreciated that the external electrical power source 22 may be operated in parallel or series resonance mode. For example, FIG. 15 shows the external power source 22 operable in a parallel resonant mode for transmitting power to the pickup coil 18 on the implanted valve. The source 20 includes an AC power source, the drive coil 22a, the capacitor 22b, and also preferably a resistive element 22c for adjusting the transmitter circuit quality factor. However, it will be understood that part of or all of the resistive element 22c may be composed of the resistance of the drive coil 22a. The circuit associated with the pickup coil 18 includes the wire 40, the capacitor 41, and the heater 20, and also preferably includes a resistive element 40b. It will be understood, however, that part of or all of the resistive element 40b may be composed of the resistance of the pickup coil 18. FIG. 16 shows operation of the power source 22 in series mode. It will be understood that other combinations of parallel and series resonance may be employed. For example, the power transmission circuit in parallel resonance mode and the power reception circuit in series resonance, or vice versa.

Figure 17:
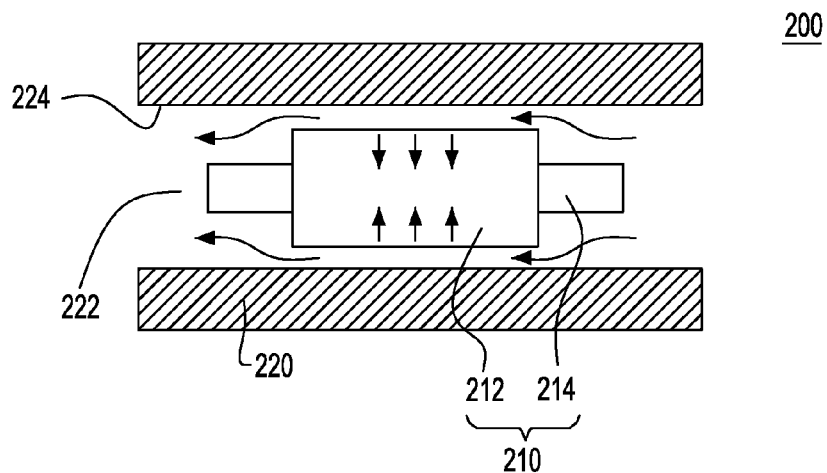
FIGS. 17 and 18 show another embodiment of an implant valve system having an internalized heating element with a thermally responsive polymer grafted thereon.
Figure 18:
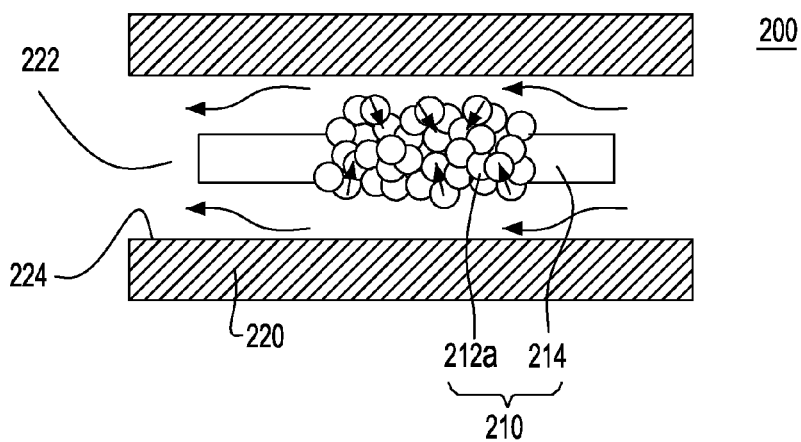

FIGS. 17 and 18 illustrate another embodiment of the present invention.

A thermally actuated valve 200 includes a thermally actuated valve element 210 and an outer bore tubing 220 having an inner wall 224 defining a lumen 222.

The valve element 210 includes an internalized heating element 214 and a thermally responsive polymer 212 grafted onto the surface of the internalized heating element 214. The internalized heating element 214 includes a glass capillary and a heating element arranged within the glass capillary.

As described in further detail below, the valve element 210 is arranged within the lumen 222 of the outer bore tubing 220 to switch the valve 200 between at least two configurations to vary a flow rate of fluid through lumen 222.

As an example, the valve element 210 is arranged within the lumen 222 of the outer bore tubing 220 to switch the valve 200 between a closed configuration and an open configuration.

In the closed configuration, the polymer 212 is at a base level temperature and is dimensioned to obstruct a flow of fluid through the lumen 222 of the outer bore tubing 220. The base level temperature can, for example, be a physiological temperature (e.g., body temperature).

By raising the temperature of the polymer 212 above the base level temperature, the valve 200 is switched from the closed configuration to an open configuration. Specifically, raising the temperature of the polymer 212 above the base level temperature will cause the polymer 212 to collapse upon the internalized heating element 214 thereby establishing an annular flow path between the polymer 212 and the inner wall 224 of the outer bore tubing 220.

A first exemplary method for fabricating the above-presented thermally actuated valve 200 is described below.

The first exemplary method of fabricating the valve 200, includes a process of preparing an internalized heating element 214. As stated above, the internalized heating element 214 can include a glass capillary upon which polymer 212 is grafted.

The glass capillary is first cleaned in a strong soap and rinsed thoroughly with water and dried. The glass capillary is then submersed in a volume of coating reagent including 1 mL of 3-(Trimethoxysilyl)propylmethacrylate in 200 mL of ethanol to which 6 mL of dilute acetic acid (1:10 glacial acetic acid:water) is added just before use. The solution is allowed to react with the glass capillary for 3 minutes, at which point the solution is poured off. The glass capillary, now modified, is then rinsed extensively with ethanol and allowed to dry. The modified glass capillary is then cut to size and placed within an outer bore tubing 220 (for example 1.75 mm i.d.) that has not been treated with 3-(trimethoxysilyl)propylmethacrylate). As an example, the outer bore tubing 220 can be a glass tube. In an exemplary configuration, the modified glass capillary can be arranged within the outer bore tubing 220 to form coaxial glass tubes.

The first exemplary method of fabricating the valve 200 further includes a process of grafting or covalently anchoring thermally responsive polymer 212 on to the surface of the internalized heating element 214 by, for example, polymerizing n-isopropylacrylamide and acrylamide-based copolymers onto the reactive monomer 3-(trimethoxysilyl)propylmethacrylate.

The above-described coaxial glass tubes are placed in a solution of n-isopropylacrylamide mixed with dimethylacrylamide and methylene bis(acrylamide). This solution is degassed under an inert atmosphere (for example, nitrogen or argon). Ammonium persulfate and N,N,N',N'-tetramethylethylenediamine are then added to polymerize the copolymer. The copolymer that forms is covalently grafted to the surface of the glass capillary 214, but is not covalently grafted onto the outer bore tubing 220. Upon raising the temperature of polymer 212, a collapse of the polymer 212 results from retention of the polymer 212 on the surface of the glass capillary 214 and detachment of the polymer 212 from the inner wall 224 of the outer bore tubing 220, forming a flow path in the resultant annulus.

An example of a process of grafting thermally responsive polymer 212 to the modified glass capillary 214 is provided herein. The above-described coaxial glass tubes are placed in a mixture of 200 microliters of n-isopropyl acrylamide (50 mg/mL), 2 microliters of methylene bis(acrylamide) (50 mg/mL), and 6 microliters of dimethylacrylamide in phosphate buffered saline solution. This solution is degassed under nitrogen for 2 hrs and 5 microliters of ammonium persulfate are added (50 mg/ml in water). The solution is stirred and 3 microliters of a 1:10 dilution of N,N,N',N'-tetramethylethylenediamine (10 microliters in 100 microliters water) are added. The reaction is allowed to proceed overnight under nitrogen purge. The coaxial glass tubes are then removed from the reaction and placed under water heated to 65° C., upon which the thermally reactive polymer 212 shrinks away from the inner wall of the outer bore tubing 220 and collapses upon the outer wall of the glass capillary. In an exemplary modification, the glass capillary and grafted polymer 212 can be removed from the outer bore tubing 220 and placed into another tube of interest.

Variation of polymer formulations can be used to adjust the actuation temperature of the thermally responsive polymer 212. For example, copolymers of poly-n-isopropyl acrylamide and dimethylacrylamide can be used to achieve transition temperatures below which the polymer 212 expands and above which it contracts, ranging from approximately 32° C. to 50° C. (0 mole fraction DMAA to 0.5 mole fraction DMAA). An exemplary embodiment for biomedical implants is a copolymer of poly-n-isopropyl acrylamide and dimethylacrylamide with a mole fraction of dimethylacrylamide of 0.3 to 0.45. This polymer formulation provides an actuation temperature ranging from approximately 38° C. to 46° C. As such, the thermally actuated valve 200 is in an expanded state at normal physiological temperature and can be actuated to collapse at temperatures slightly above physiological temperature.

A second exemplary method of fabricating the above-described thermally actuated valve 200 is provided herein. As illustrated in FIG. 18, the second exemplary fabrication method includes generating copolymers 212a of thermally responsive polymers using surfactant free polymerization and grafting the resultant spherical copolymers 212a onto the internalized heating element 214. One approach is to mix solutions of n-isopropylacrylimide and acrylic acid with methylene bis(acrylamide) and to purge the solution with nitrogen. Ammonium persulfate is then added and the solution is stirred and elevated to 70° C. under an inert environment. This results in the generation of spherical polymers 212a which can then be covalently grafted onto the surface of an internalized heating element 214. In this case, the copolymerization of acrylic acid provides carboxylic acid groups which can be grafted onto primary amines using carbodiimide chemistry. For example, the glass surface of the internalized heating element 214 can be functionalized by vapor or liquid priming with 3-aminopropyltriethoxysilane (APTES) to provide pendant primary amines. An amide bond can then be formed between the pendant amine and the carboxylic acid of the pnipam-co-paa polymer microspheres using the crosslinking agent, 1-ethyl-3-(3-dimethylaminopropyl)carbodiimide. In this configuration, the spheroids of thermally responsive polymer 212a are immobilized onto the surface of the internalized heating element 214. If the resulting thermally activated valve element 210 is placed within another tube of interest, the expansion and collapse of the spheroids of thermally responsive polymer 212a results in decreasing and increasing flow, respectively, through the tube of interest in response to cooling and heating and heating of the spheroids of thermally responsive polymer 212a.

Figure 19:
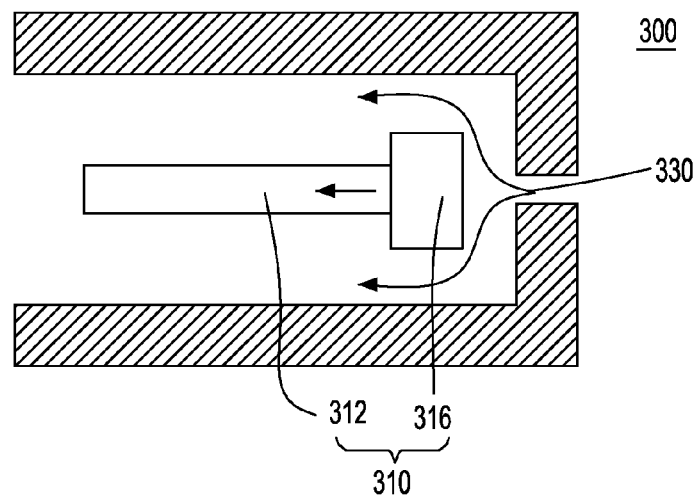
FIG. 19 shows another embodiment of an implant valve system having a valve element including a thermally responsive polymer and a solid element attached thereon.

FIG. 19 illustrates another embodiment of the present invention.

A thermally activatable valve 300 includes a valve element 310 further including a thermally responsive polymer 312 and a solid element 316 attached to the polymer 312. The valve element 310 is arranged in proximity to a valve seat taking the form of a fluidic inlet/outlet 330. The valve element 310 is configured to switch the valve 300 between at least a closed configuration and an open configuration.

In the closed configuration, the polymer 312 of valve element 310 is in an expanded state and dimensioned to urge solid element 316 against fluidic inlet/outlet 330 to restrict the flow of fluid through fluidic inlet/outlet 330.

Upon heating of the polymer 312, the valve element 310 switches the thermally actuated valve 300 to an open configuration. Specifically, upon heating, the polymer 312 will collapse to remove the solid element 316 from the fluidic inlet/outlet 330 thereby causing less flow restriction to the fluidic inlet/outlet 330.

Exemplary configurations of structural features for actuating the valve 300 is described below.

In a first configuration, the valve 300 can be actuated by Joule heating. Conductive materials may be placed in thermal contact with the polymer 312. For example, conductive materials may be placed within, around, and/or enmeshed in the polymer 312. Passage of DC or AC current through the conductive materials release heat, thereby raising the temperature of the conductive materials and the polymer 312.

In a second configuration, the valve 300 can be actuated by induction heating. Conductive material may be placed in thermal contact with the polymer 312. The conductive material is heated by electromagnetic induction, where eddy currents are generated within the conductive material and resistance leads to Joule heating of the conductive material.

The conductive material may be a continuous conductive material internal or external to the polymer 312, or the conductive material may be discontinuous conductive materials embedded within or around the polymer 312 such as discrete nano- and microspheres of metals or metallic conductors. Induction heating may also be utilized by incorporating conductive material within or around the polymer 312 such as within a glass encapsulated internal heater as described above.

Magnetic materials may be incorporated within, around, or enmeshed in the polymer 312 to provide heating via induction heating. These magnetic materials may include nano- and microparticles of magnetic materials which are heated by inductive heating. These magnetic materials may include Curie thermoregulated materials such that heating can be controlled by the transition of these magnetic materials from ferro/feri magnetic below the Curie point to paramagnetic above the Curie temperature.

In a third configuration, the valve 300 can be actuated by ultrasonic excitation. Ultrasonic energy is focused on or around the valve 300 to generate heat in the tissue surrounding, or the materials including and surrounding the valve 300.

Enhanced heating can be achieved by placing ultrasound contrast agents surrounding the polymer 312 such that the absorption of ultrasonic energy is enhanced in the region surrounding the polymer 312.

An embodiment for medical implantation is to place the valve element 310 within the lumen of a tube which in turn is surrounded by an inflatable balloon. To deploy the system as an implant, the system is placed in the desired tissue and the balloon is then inflated with an ultrasound contrast agent or any material which has higher absorbance of ultrasound energy than human tissue. The inflation media can then be used as a target for enhanced absorption of ultrasound excitation, and will therefore be heated more effectively than surrounding tissue. Heating of the inflation media can then be used to actuate the embedded polymer 312.

In a fourth configuration, the valve 300 can be actuated by infrared or near-infrared heating. In particular, near-infrared heating may be beneficial due to the significant tissue penetration depth of near infrared at wavelengths within a therapeutic window of 700-1200 nm.

As an example of near infrared heating, gold nanospheres are incorporated into the polymeric matrix, or packed in an internal heating tube within a valve element 310. These gold nanospheres may then be heated by near infrared energy, including multiphoton excitation of multiple convergent rays of near infrared radiation.

In a fifth configuration, the valve 300 can be actuated by physiological situations. Examples of physiological situations that can be harness to actuate the valve 300 include, but are not limited to, elevated body temperatures due to fever, infection, microbial process, increased activity/metabolism of cells and tissue including exercise and physical exertion, and increased growth/proliferation/metabolism of cells, including tumore cells.

In a sixth configuration, the valve 300 can be actuated by convective or conductive heating of the tissue surrounding the valve 300.

Another embodiment of the present invention will be described below with reference to the above-presented embodiments.

The thermally reactive polymer valve systems described in the above-presented embodiments can be modified to be in either a normally closed or a normally open state. For example, a copolymer formulation of 30% mole fraction dimethylacrylamide and 70% n-isopropylacrylamide will provide an expanded polymer at normal physiological temperature (37° C.) that will collapse upon delivery of heat to raise the polymer temperature to 38° C. In a contrasting example, a polymer including only poly-n-isopropyl acrylamide will be in a collapsed state at physiological temperature, but will be in an expanded state when cooled.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

It will be appreciated that the valve systems of the various embodiments described herein may be suitably configured for use in the treatment and study of CDH as well as other conditions wherein treatment or study involves controlling the flow of fluid in physiological channels. These other conditions include, for example, delivery of therapeutic agents, the movement of reproductive materials in the reproductive tracts or males and females, blood flow to male reproductive organs, the release of bile from the gall bladder or liver, the release of insulin from the pancreas.

What is claimed is:

1. A thermally actuated valve comprising:
   a tubing;
   an expandable lumen arranged adjacent to an interior sidewall of the tubing;
   a thermally responsive polymer arranged within the expandable lumen; and
   a thermal actuating element comprising a coil wire and a resistance heater electrically connected to the coil wire, wherein in response to an external electrical field, a current is induced in the coil wire to power the resistance heater to heat the thermally responsive polymer to switch the thermally responsive polymer between a swollen state that expands the lumen and a shrunken state that deflates the lumen to vary a flow rate of fluid through the tubing.

2. The thermally actuated valve of claim 1, wherein the thermally responsive polymer is anchored to the expandable lumen to form an annulus defining a variable flow path through the open region of the annulus.

3. A valve implant system comprising:
   a thermally activated valve comprising:
      a tubing;
      an expandable lumen arranged adjacent to an interior sidewall of the tubing; and
      a thermally responsive polymer arranged within the expandable lumen;
   a thermal actuating element comprising a coil wire and a resistance heater electrically connected to the coil wire, wherein in response to an external electrical field, a current is induced in the coil wire to power the resistance heater to heat the thermally responsive polymer to switch the thermally responsive polymer between a swollen state that expands the lumen and a shrunken state that deflates the lumen to vary a flow rate of fluid through the tubing;
   an inlet in communication with a first opening of the tubing of the thermally activated valve; and
   an outlet in communication with a second opening of the tubing of the thermally activated valve.

4. The valve implant system of claim 3, wherein the thermally responsive polymer is anchored to the expandable lumen to form an annulus defining a variable flow path through the open region of the annulus.

5. The thermally actuated valve of claim 1, wherein the resistance heater comprises a thin-film metal resistance heater patterned to the tubing.

6. The thermally actuated valve of claim 1, wherein the resistance heater comprises a resistance wire wrapped around the tubing.

7. The thermally actuated valve of claim 1, wherein the lumen comprises a membrane or perforation for allowing fluid to be expelled or absorbed by the thermally responsive polymer.

8. The valve implant system of claim 3, wherein the resistance heater comprises a thin-film metal resistance heater patterned to the tubing.

9. The valve implant system of claim 3, wherein the resistance heater comprises a resistance wire wrapped around the tubing.

10. The valve implant system of claim 3, wherein the lumen comprises a membrane or perforation for allowing fluid to be expelled or absorbed by the thermally responsive polymer.

* * * * *